(12) United States Patent
Kawakami et al.

(10) Patent No.: US 8,696,604 B2
(45) Date of Patent: Apr. 15, 2014

(54) MUSCLE FORCE ASSISTING DEVICE AND ITS OPERATING METHOD

(75) Inventors: Takashi Kawakami, Ehime (JP); Toshihiko Ishiko, Ehime (JP); Keisuke Ueda, Osaka (JP)

(73) Assignee: Panasonic Corporation, Osaka (JP)

( * ) Notice: Subject to any disclaimer, the term of this patent is extended or adjusted under 35 U.S.C. 154(b) by 869 days.

(21) Appl. No.: 12/810,601

(22) PCT Filed: Dec. 11, 2008

(86) PCT No.: PCT/JP2008/003706
§ 371 (c)(1),
(2), (4) Date: Jun. 25, 2010

(87) PCT Pub. No.: WO2009/084161
PCT Pub. Date: Jul. 9, 2009

(65) Prior Publication Data
US 2010/0280425 A1    Nov. 4, 2010

(30) Foreign Application Priority Data

Dec. 28, 2007    (JP) .................................. 2007-340672

(51) Int. Cl.
*A61H 1/00* (2006.01)
*A61H 1/02* (2006.01)
*A61H 5/00* (2006.01)

(52) U.S. Cl.
USPC ...................... 601/5; 601/23; 601/33; 601/34

(58) Field of Classification Search
CPC ........... A61H 3/008; A61H 2201/5007; A61H 2201/1238; A61H 1/0237; A61H 1/0274; A61H 1/02; A61H 1/0255; A61H 1/0288; A61H 1/0259; A61H 1/0285; A61H 1/0281; A61H 1/0214; A61H 1/024; A61H 1/0244; A61H 23/0254; A61H 2303/0456; B25J 9/0006; A63B 21/0058; A63B 21/0004; A63B 23/0494; A63B 23/16; A63B 2220/16
USPC .......................... 601/5, 23, 33, 34, 35, 40, 27
See application file for complete search history.

(56) References Cited

U.S. PATENT DOCUMENTS 3,707,963 A * 1/1973 Keropian ........................ 602/21
4,739,692 A * 4/1988 Wassam et al. ................... 91/36
(Continued)

FOREIGN PATENT DOCUMENTS

JP    52-40378        9/1975
JP    5-88523 U    12/1993
(Continued)

OTHER PUBLICATIONS

International Search Report for PCT/JP2008/003706, Mar. 3, 2009.

*Primary Examiner* — Justine Yu
*Assistant Examiner* — Colin W Stuart
(74) *Attorney, Agent, or Firm* — RatnerPrestia (57) ABSTRACT

A muscle force assisting can increase a bending angle of a second attachment with respect to a first attachment. The muscle force assisting device includes the first attachment arranged along one bone of a joint, the second attachment arranged along the other bone of the joint, and an artificial muscle having one end provided on the first attachment and having the other end provided on the second attachment, an actuator that is extensible or contractible by supplying or discharging a substance such as gas, liquid and solid, or a mixture thereof is used as the artificial muscle, and the muscle force assisting device assists motion of a user's elbow, knee and wrist, the one end of the artificial muscle can be displaced with respect to the first attachment, the one end of the artificial muscle is displaced, and a bending angle of the second attachment with respect to the first attachment is increased as compared with a case where the one end of the artificial muscle is not displaced.

8 Claims, 8 Drawing Sheets

(56) References Cited

U.S. PATENT DOCUMENTS

| | | | |
|---|---|---|---|
| 5,013,037 A * | 5/1991 | Stermer | 482/122 |
| 5,351,602 A * | 10/1994 | Monroe | 92/64 |
| 5,364,323 A * | 11/1994 | Liu | 482/45 |
| 6,689,074 B2 * | 2/2004 | Seto et al. | 601/5 |
| 2004/0267331 A1 * | 12/2004 | Koeneman et al. | 607/49 |
| 2007/0129653 A1 * | 6/2007 | Sugar et al. | 601/5 |
| 2007/0144299 A1 * | 6/2007 | Okazaki | 74/490.1 |
| 2008/0195005 A1 * | 8/2008 | Horst et al. | 601/22 |

FOREIGN PATENT DOCUMENTS

| | | |
|---|---|---|
| JP | 2004-105263 A | 4/2004 |
| JP | 2006-192529 A | 7/2006 |
| JP | 2007-167484 A | 7/2007 |
| JP | 3984641 B2 | 10/2007 |
| WO | WO 2007-043308 A1 | 4/2007 |

\* cited by examiner

MUSCLE FORCE ASSISTING DEVICE AND ITS OPERATING METHOD

This application is a U.S. NATIONAL PHASE APPLICATION OF PCT INTERNATIONAL APPLICATION No. PCT/JP2008/003706.

TECHNICAL FIELD

The present invention relates to a muscle force assisting device that assists motion of a user's elbow, knee, and wrist using an actuator that is extensible or contractible by supplying or discharging a substance such as gas, liquid and solid, or a mixture thereof.

BACKGROUND TECHNIQUE

There has already been proposed a power device including a tube that is characterized in that if a substance such as gas, liquid and solid, or a mixture thereof is infused into the tube, a size thereof in its longitudinal direction is restrained but it expands in its radial direction, a cylindrical sleeve that is extensible or contractible in its longitudinal direction and radial direction is disposed outside the tube, both ends of the tube are restrained, an inlet is formed in one of the ends, and a film or fiber made of polyester-based, polyamide-based, polyethylene-based, polyimide-based, polystyrene-based, polycarbonate-based substance or mixture thereof is used as the tube (patent documents 1 and 2).

Further, a motion-assisting device utilizing this kind of power device is also proposed (patent documents 3 and 4).

[Patent Document 1] Japanese Patent Application Laid-open No. 2004-105263

[Patent Document 2] Japanese Patent Application Laid-open No. S52-40378

[Patent Document 3] PCT Application Laid-open No. 2007/043308

[Patent Document 4] Japanese Patent Application Laid-open No. 2007-167484

DISCLOSURE OF THE INVENTION

However, if the MaKibben air pressure actuator utilized in the above documents is used, the following problem occurs.

Generally, the MaKibben air pressure actuator has an excellent shrinkage, but this shrinkage is inferior to that of a muscle of a human body.

Therefore, when an artificial muscle such as the MaKibben air pressure actuator is utilized, if it is disposed at the same location as the muscle of the human body, the same or more excellent bending angle can not be obtained.

A case where this kind of artificial muscle is utilized for bending an elbow will be described using FIGS. 6 to 8.

Figure 6:
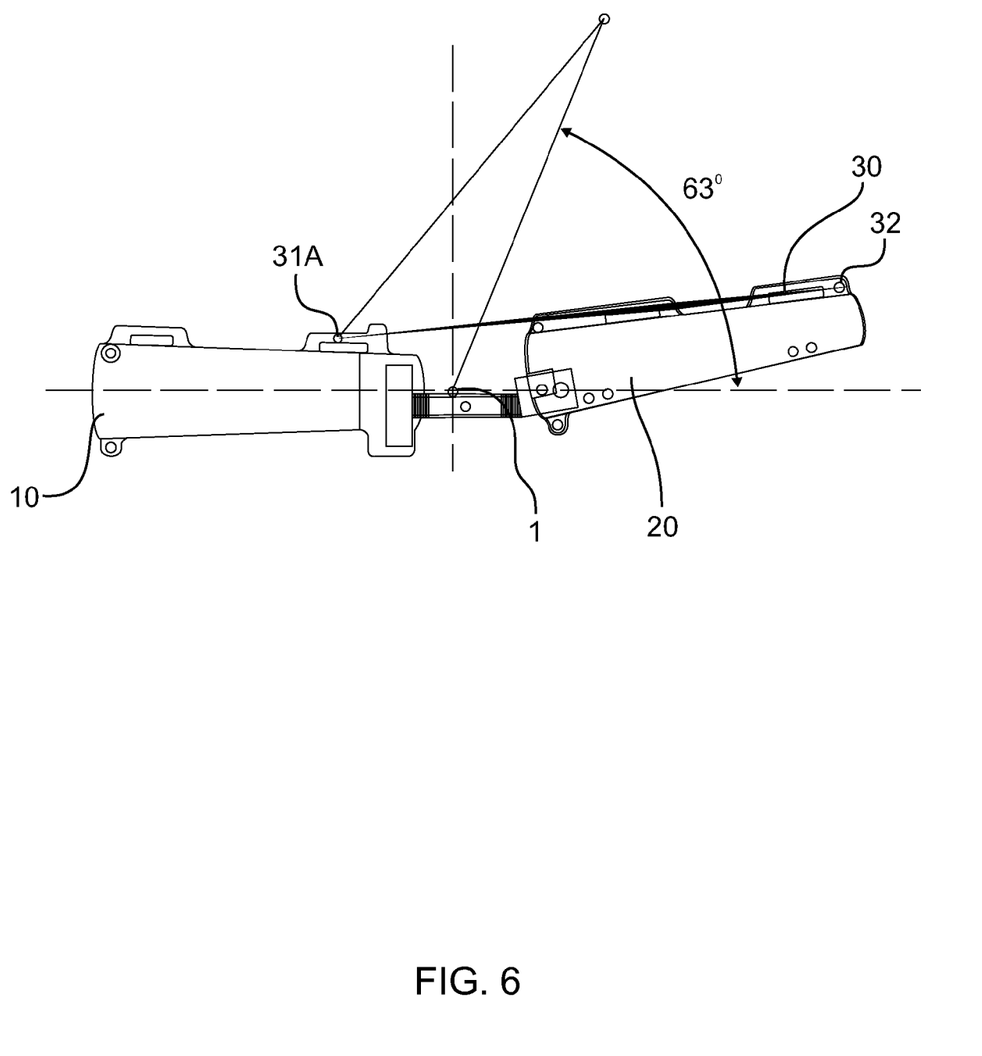
FIG. 6 is a diagram of a configuration showing a comparative example 1.
Figure 7:
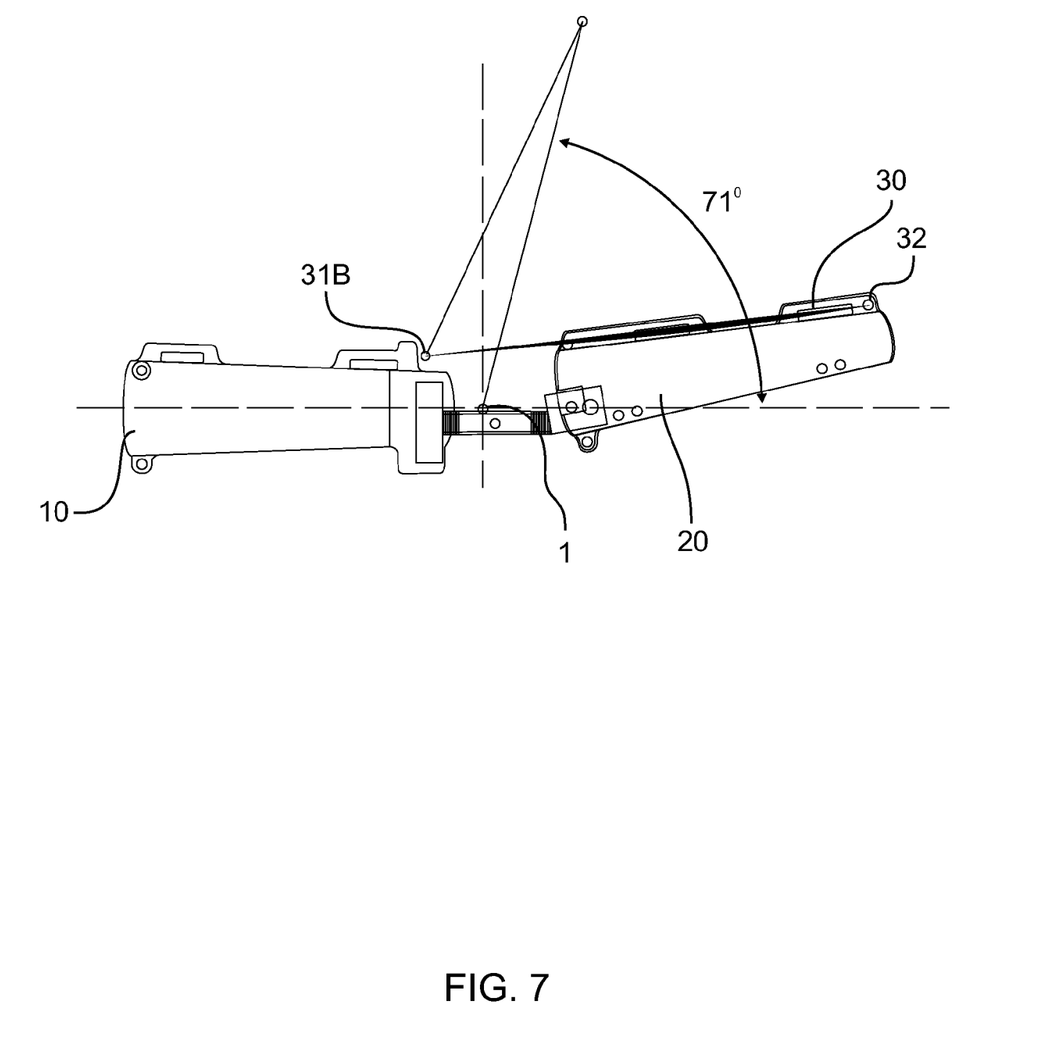
FIG. 7 is a diagram of a configuration showing a comparative example 2.
Figure 8:
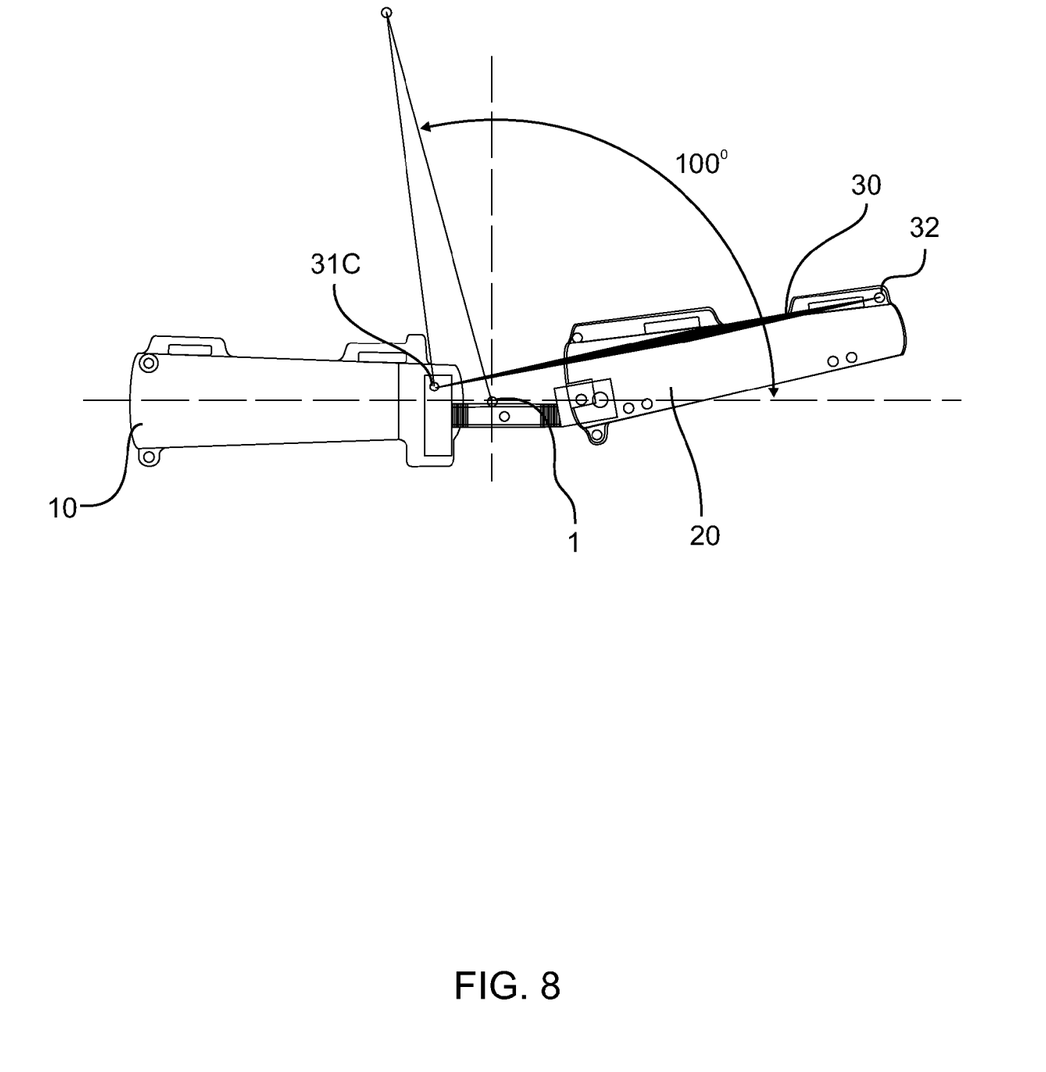
FIG. 8 is a diagram of a configuration showing a comparative example 3.

FIG. 6 shows a configuration of a comparative example 1, FIG. 7 shows a configuration of a comparative example 2, and FIG. 8 shows a configuration of a comparative example 3.

In FIGS. 6 to 8, the muscle force assisting device includes a first attachment 10 attached to an upper arm, a second attachment 20 attached to a forearm, and an artificial muscle 30 having one end provided on the first attachment 10 and having the other end provided on the second attachment 20.

An initial angle between the first attachment 10 and the second attachment 20 is set to 10°, and a shrinkage of the artificial muscle 30 in its attached state is set to 22%.

In the following description, a phantom line passing through a turning axis 1 of the joint and extending along a longitudinal direction of the first attachment 10 is defined as an X-axis, a phantom line passing through the turning axis 1 of the joint and extending perpendicular to the X-axis is defined as a Y-axis, and a bending direction of the second attachment 20 with respect to an intersection (turning axis 1) between the X-axis and the Y-axis is defined as a plus direction of the Y-axis.

In the comparative example 1 shown in FIG. 6, one end 31A of the artificial muscle 30 is located on an upper end of the first attachment 10 on the side of the joint, and the other end 32 of the artificial muscle 30 is located on an upper end of the second attachment 20 on the opposite side from the joint.

As shown in FIG. 6, if the one end 31A of the artificial muscle 30 is separated from the turning axis 1 of the joint by a predetermined distance, a driving force that is necessary for bending the second attachment 20 with respect to the first attachment 10 can be generated by contracting the artificial muscle 30, but the bending angle of the second attachment 20 with respect to the first attachment 10 is reduced. In the case of this comparative example, the bending angle with respect to the X-axis is 63°, and a driving force required for bending is 87N.

In the comparative example 2 shown in FIG. 7, one end 31B of the artificial muscle 30 is closer to the Y-axis than the one end 31A of the artificial muscle 30 shown in FIG. 6, and the other end 32 of the artificial muscle 30 is located at the same position as that of the comparative example 1.

As shown in FIG. 7, if the one end 31B of the artificial muscle 30 is close to the turning axis 1 of the joint, the bending angle can be increased as compared with the comparative example 1. However, the driving force required for maximum bending the second attachment 20 with respect to the first attachment 10 is increased. In the case of the comparative example 2, the bending angle with respect to the X-axis is 71°, and the driving force required for bending is 90N.

In the comparative example 3 shown in FIG. 8, one end 31C of the artificial muscle 30 is closer to the X-axis than the one end 31B of the artificial muscle 30 shown in FIG. 7, and the other end 32 of the artificial muscle is located at the same position as that of the other comparative examples.

If the one end 31C of the artificial muscle 30 is set closer to the turning axis 1 of the joint as shown in FIG. 8, the bending angle can be increased as compared with the comparative example 2, but the driving force required for bending the second attachment 20 to the utmost with respect to the first attachment 10 is further increased. In the case of the comparative example 3, the bending angle with respect to the X-axis is 100°, and the driving force required for bending is 219N.

If the mounting position of the artificial muscle 30 that increases the bending angle is employed, a force required for bending is increased, and if the driving force required for bending becomes greater than a driving force of the artificial muscle 30, it can not be bent.

If the one end 31C of the artificial muscle 30 is too close to the turning axis 1 of the joint, the driving force of the artificial muscle 30 does not function for the bending motion, and this force only brings the second attachment 20 closer to the turning axis 1 of the joint.

When the first attachment 10 and the second attachment 20 are connected to each other through one rotation shaft, even if the one end 31 of the artificial muscle 30 is brought close to the rotation shaft, the driving force required for bending can reliably be generated.

In this case, however, if the turning axis 1 of the joint, a rotation shaft of the first attachment 10 and a rotation shaft of the second attachment 20 are deviated from each other when the artificial muscle is worn, or if the turning axis 1 of the joint, the rotation shaft of the first attachment 10 and the rotation shaft of the second attachment 20 are deviated from each other as a result of the bending motion after the artificial muscle is worn, there is a problem that an excessive load is applied to a user.

Further, a joint of a human body does not turn exactly around one axis, if the first attachment 10 and the second attachment 20 are connected to each other through the one rotation shaft, the turning axis 1 of the joint and the rotation shafts of the first attachment 10 and the second attachment 20 can not completely coincide with each other at the time of the bending motion.

Therefore, it is not preferable to connect the first attachment 10 and the second attachment 20 through the one rotation shaft, but when the first attachment 10 and the second attachment 20 are not connected to each other through the one rotation shaft, the one end 31 of the artificial muscle 30 can not be brought close to the turning axis 1 of the joint, and there is a problem that a sufficient bending angle can not be secured.

The present invention has been accomplished to solve such a conventional problem, and it is an object of the invention to provide a muscle force assisting device capable of increasing a bending angle of the second attachment with respect to the first attachment.

MEANS FOR SOLVING THE PROBLEM

A first aspect of the present invention provides a muscle force assisting device comprising a first attachment arranged along one bone of a joint, a second attachment arranged along the other bone of the joint, and an artificial muscle having one end provided on the first attachment and having the other end provided on the second attachment, in which an actuator that is extensible or contractible by supplying or discharging a substance such as gas, liquid and solid, or a mixture thereof is used as the artificial muscle, and the muscle force assisting device assists motion of a user's elbow, knee and wrist, wherein the one end of the artificial muscle can be displaced with respect to the first attachment, the one end of the artificial muscle is displaced, and a bending angle of the second attachment with respect to the first attachment is increased as compared with a case where the one end of the artificial muscle is not displaced.

According to a second aspect of the invention, in the muscle force assisting device of the first aspect, the first attachment includes a swing arm, an end of the swing arm on a side opposite from a joint is a turning fulcrum, and an end of the swing arm on a side of the joint is a displacing end, and the one end of the artificial muscle is provided on the displacing end of the swing arm.

According to a third aspect of the invention, the muscle force assisting device of the second aspect further comprises an auxiliary artificial muscle having one end provided on the first attachment and having the other end provided on the displacing end of the swing arm.

According to a fourth aspect of the invention, in the muscle force assisting device of the second or third aspect, the first attachment includes a guide plate, the guide plate includes a guide hole, and the displacing end of the swing arm is displaced along the guide hole.

According to a fifth aspect of the invention, in the muscle force assisting device of the third aspect, when a phantom line passing through a turning axis of the joint and extending along a longitudinal direction of the first attachment is defined as an X-axis, and a phantom line passing through the turning axis of the joint and extending perpendicular to the X-axis is defined as a Y-axis, and when a bending direction of the second attachment with respect to an intersection between the X-axis and the Y-axis is defined as a plus direction of the Y-axis, the turning fulcrum of the swing arm is disposed at a plus position of the Y-axis, and one end of the auxiliary artificial muscle is disposed at a minus position of the Y-axis.

According to a sixth aspect of the invention, in the muscle force assisting device of the third aspect, when a phantom line passing through a turning axis of the joint and extending along a longitudinal direction of the first attachment is defined as an X-axis, and a phantom line passing through the turning axis of the joint and extending perpendicular to the X-axis is defined as a Y-axis, and when a bending direction of the second attachment with respect to an intersection between the X-axis and the Y-axis is defined as a plus direction of the Y-axis, the turning fulcrum of the swing arm is disposed at a plus position of the Y-axis, one end of the auxiliary artificial muscle is disposed at a minus position of the Y-axis, and the displacing end of the swing arm is displaced between the plus position of the Y-axis and the minus position of the Y-axis.

According to a seventh aspect of the invention, in the muscle force assisting device of the first aspect, the first attachment and the second attachment are connected to each other through a spring joint, and a coil spring is used as the spring joint.

An eighth aspect of the invention provides an operating method of the muscle force assisting device of the third aspect comprising a first power source that contracts the artificial muscle, and a second power source that contracts the auxiliary artificial muscle, wherein at the time of bending motion, operation of the first power source is started before operation of the second power source is started.

According to the invention, it is possible to increase the bending angle of the second attachment with respect to the first attachment.

BEST MODE FOR CARRYING OUT THE INVENTION

In the muscle force assisting device of the first aspect of the invention, the one end of the artificial muscle can be displaced with respect to the first attachment. By displacing the one end of the artificial muscle, the bending angle of the second attachment with respect to the first attachment is increased as compared with a case where the one end of the artificial muscle is not displaced. With this aspect, the bending angle can be increased by displacing the one end of the artificial muscle without increasing the driving force that is required for bending.

According to the second aspect of the invention, in the muscle force assisting device of the first aspect, the first attachment includes a swing arm, an end of the swing arm on a side opposite from a joint is a turning fulcrum, and an end of the swing arm on a side of the joint is a displacing end, and the one end of the artificial muscle is provided on the displacing end of the swing arm. With this aspect, the one end of the artificial muscle can be displaced by providing the one end of the artificial muscle on the displacing end of the swing arm.

According to the third aspect of the invention, the muscle force assisting device of the second aspect further comprises an auxiliary artificial muscle having one end provided on the first attachment and having the other end provided on the displacing end of the swing arm. With this aspect, the bending angle of the artificial muscle can be increased by displacing the swing arm by the auxiliary artificial muscle.

According to the fourth aspect of the invention, in the muscle force assisting device of the second or third aspect, the first attachment includes a guide plate, the guide plate includes a guide hole, and the displacing end of the swing arm is displaced along the guide hole. With this aspect, by displacing the swing arm along the guide hole, the swing arm can be displaced stably.

According to the fifth aspect of the invention, in the muscle force assisting device of the third aspect, when a phantom line passing through a turning axis of the joint and extending along a longitudinal direction of the first attachment is defined as an X-axis, and a phantom line passing through the turning axis of the joint and extending perpendicular to the X-axis is defined as a Y-axis, and when a bending direction of the second attachment with respect to an intersection between the X-axis and the Y-axis is defined as a plus direction of the Y-axis, the turning fulcrum of the swing arm is disposed at a plus position of the Y-axis, and one end of the auxiliary artificial muscle is disposed at a minus position of the Y-axis. With this aspect, the movable range of the swing arm can be increased, and the swing arm can be moved smoothly by the auxiliary artificial muscle.

According to the sixth aspect of the invention, in the muscle force assisting device of the third aspect, when a phantom line passing through a turning axis of the joint and extending along a longitudinal direction of the first attachment is defined as an X-axis, and a phantom line passing through the turning axis of the joint and extending perpendicular to the X-axis is defined as a Y-axis, and when a bending direction of the second attachment with respect to an intersection between the X-axis and the Y-axis is defined as a plus direction of the Y-axis, the turning fulcrum of the swing arm is disposed at a plus position of the Y-axis, one end of the auxiliary artificial muscle is disposed at a minus position of the Y-axis, and the displacing end of the swing arm is displaced between the plus position of the Y-axis and the minus position of the Y-axis. With this aspect, the movable range of the swing arm can be increased, and the swing arm can be moved smoothly by the auxiliary artificial muscle.

According to the seventh aspect of the invention, in the muscle force assisting device of the first aspect, the first attachment and the second attachment are connected to each other through a spring joint, and a coil spring is used as the spring joint. With this aspect, the coil spring constitutes the joint, and even if the muscle force assisting device and the joint are deviated from each other, smooth motion can be secured.

According to the eighth aspect of the invention, the operating method of the muscle force assisting device described in the third aspect comprises a first power source that contracts the artificial muscle, and a second power source that contracts the auxiliary artificial muscle, and at the time of bending motion, operation of the first power source is started before operation of the second power source is started. With this aspect, after the operation of the artificial muscle is started, the one end of the artificial muscle is displaced and thus, smooth motion can be carried out.

EMBODIMENT

An embodiment of the muscle force assisting device according to the present invention will be described.

Figure 1A:
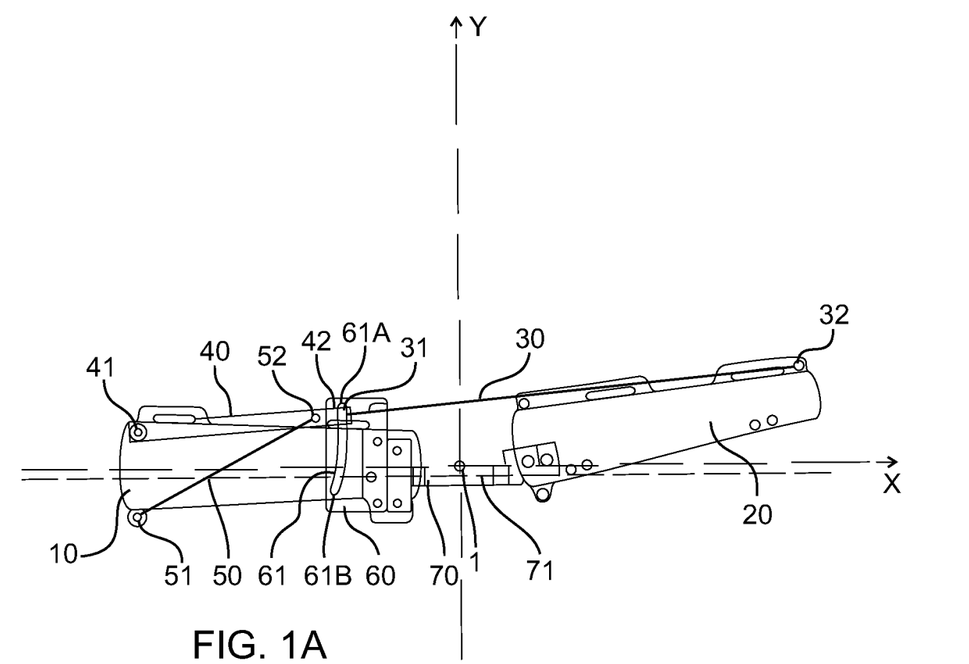
FIGS. 1(a) and 1(b) are diagrams of a configuration showing a stretched state of a muscle force assisting device according to an embodiment of the present invention.
Figure 1B:
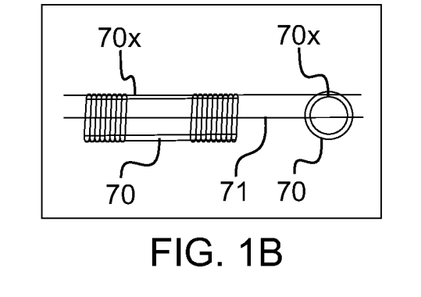
Figure 2:
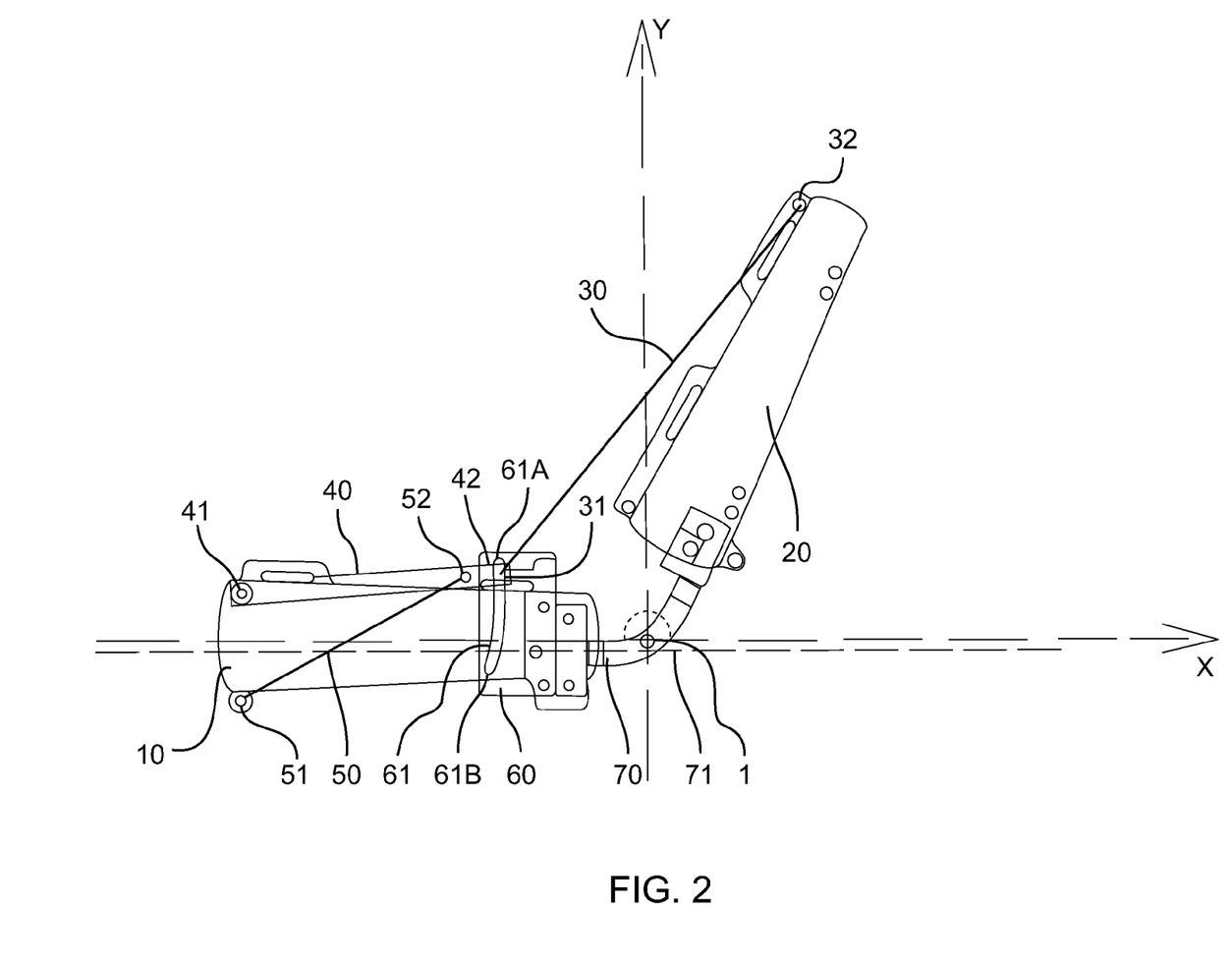
FIG. 2 is a diagram of a configuration showing a halfway state of bending motion of the muscle force assisting device.
Figure 3:
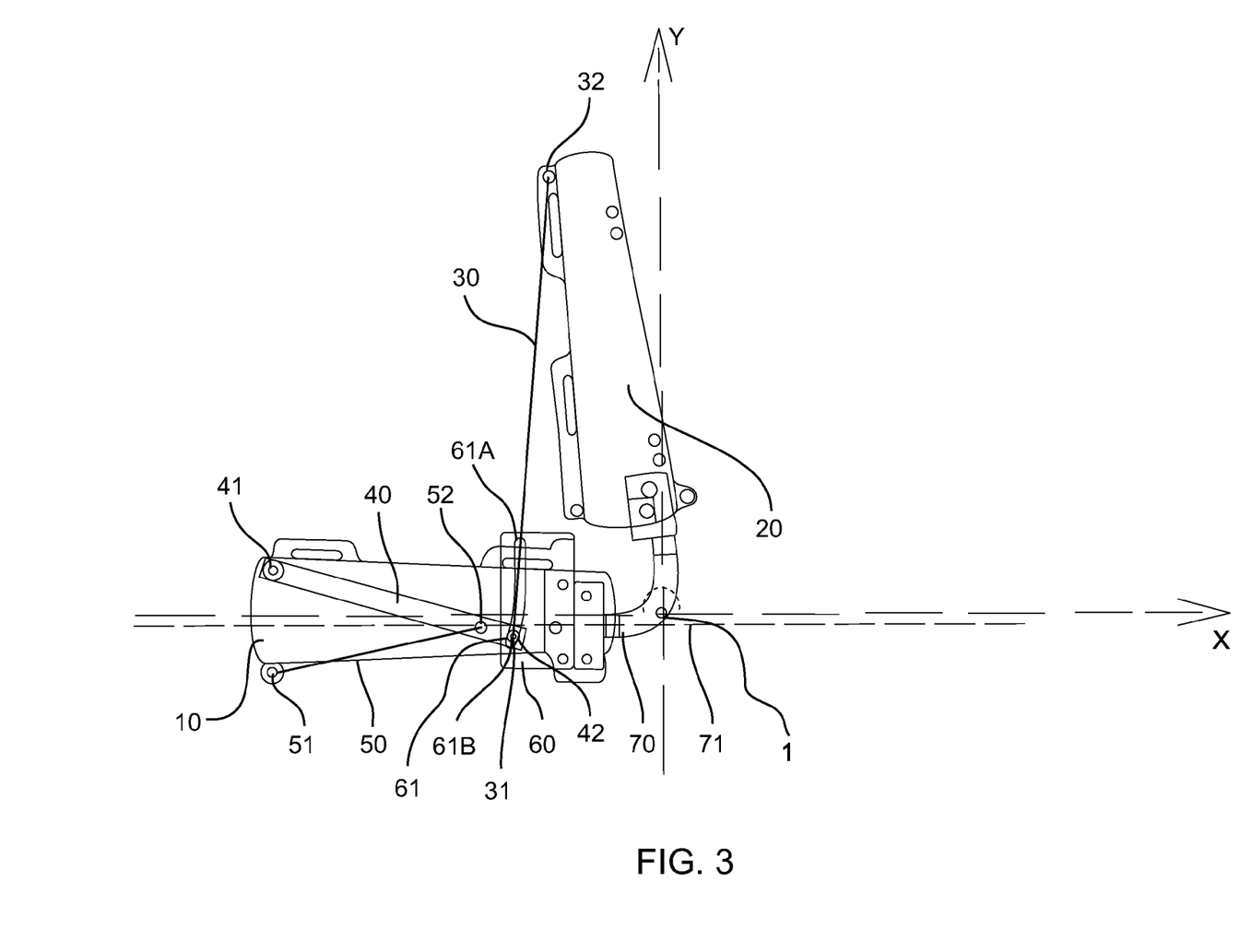
FIG. 3 is a diagram of a configuration showing a bent state of the muscle force assisting device.
Figure 4:
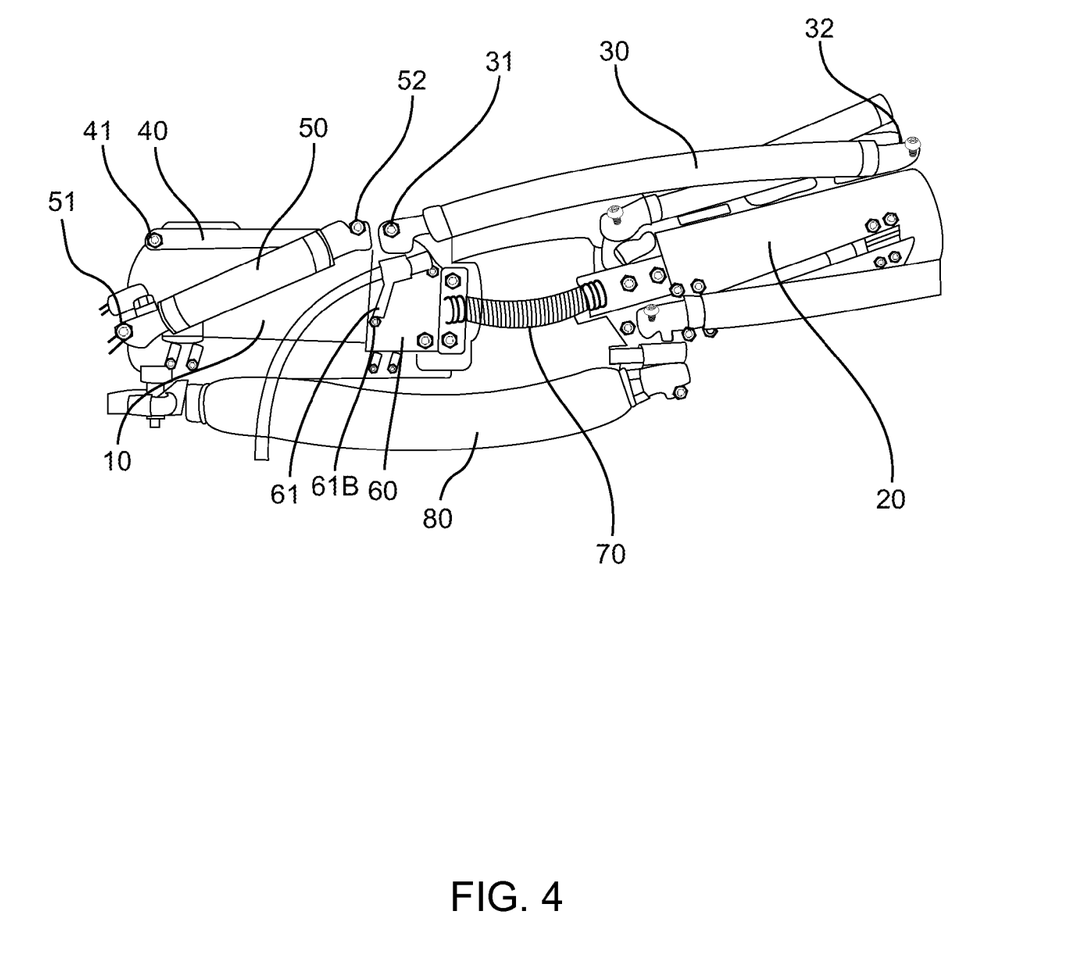
FIG. 4 is a perspective view of essential portions of the muscle force assisting device corresponding to FIGS. 1(a) and 1(b)
Figure 5:
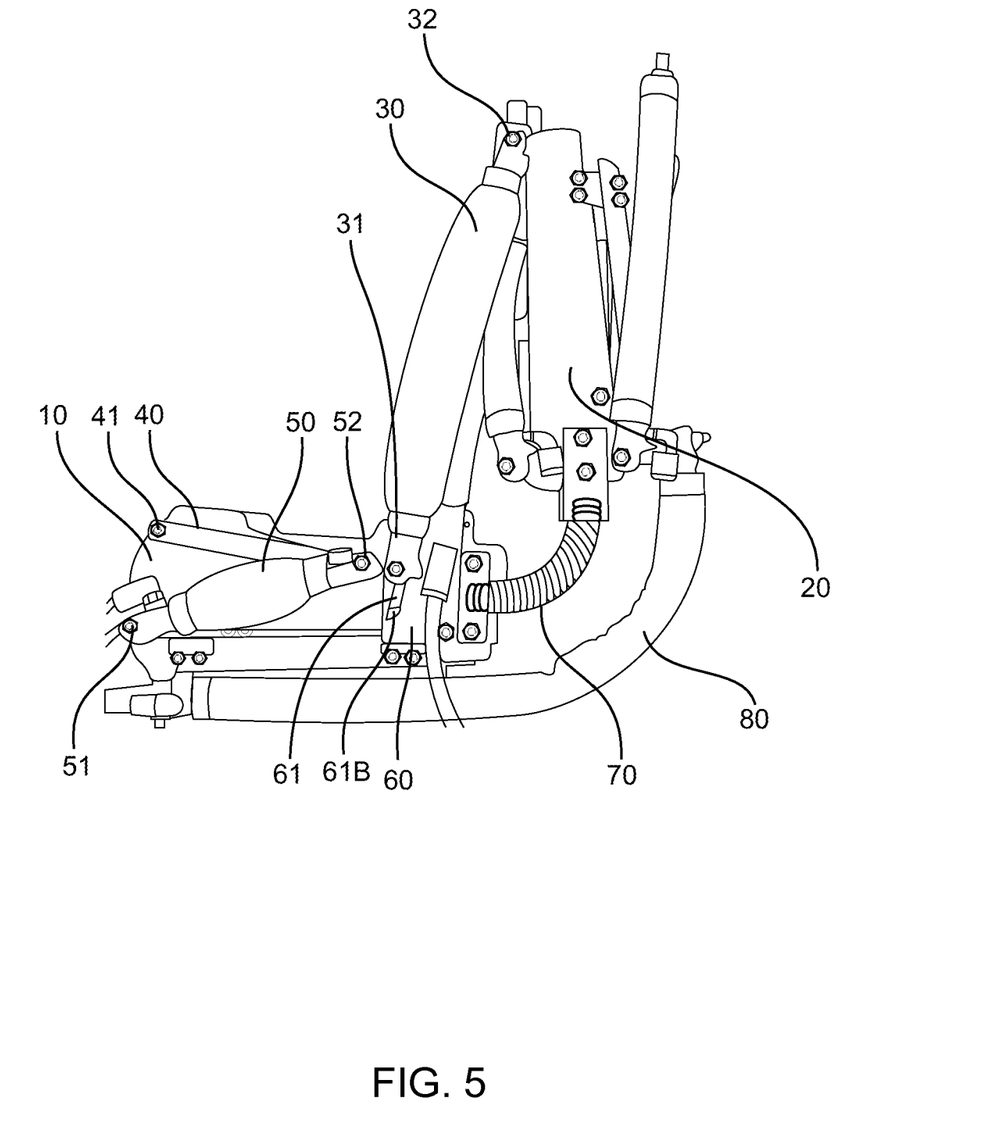
FIG. 5 is a perspective view of essential portions of the muscle force assisting device corresponding to FIG. 3.

FIGS. 1(a) and 1(b) are diagrams of a configuration showing a stretched state of a muscle force assisting device according to an embodiment of the present invention. FIG. 2 is a diagram of a configuration showing a halfway state of bending motion of the muscle force assisting device. FIG. 3 is a diagram of a configuration showing a bent state of the muscle force assisting device. FIG. 4 is a perspective view of essential portions of the muscle force assisting device corresponding to FIGS. 1(a) and 1(b). FIG. 5 is a perspective view of essential portions of the muscle force assisting device corresponding to FIG. 3.

The muscle force assisting device of the embodiment includes a first attachment 10 arranged along one bone of a joint, a second attachment 20 arranged along the other bone of the joint, and a artificial muscle 30 having one end 31 provided on the first attachment 10, and having the other end 32 provided on the second attachment 20.

When the artificial muscle is attached to an elbow as in this embodiment, the first attachment 10 is attached to an upper arm, and the second attachment 20 is attached to a forearm.

The artificial muscle 30 is an actuator that is extensible or contractible at least in its longitudinal direction by supplying or discharging a substance such as gas, liquid and solid, or a mixture thereof.

The first attachment 10 has a swing arm 40. An end of the swing arm 40 on a side opposite from the joint is a turning fulcrum 41, and an end of the swing arm 40 on the side of the joint is a displacing end 42. The one end 31 of the artificial muscle 30 is provided on the displacing end 42 of the swing arm 40.

The first attachment 10 includes an auxiliary artificial muscle 50. One end 51 of the auxiliary artificial muscle 50 is provided on an end of the first attachment 10 opposite from the joint, and the other end 52 is provided on the displacing end 42 of the swing arm 40.

The first attachment 10 includes a guide plate 60. The guide plate 60 has a guide hole 61, and the displacing end 42 of the swing arm 40 is displaced along the guide hole 61.

In the following description, a phantom line passing through a turning axis 1 of the joint and extending along a longitudinal direction of the first attachment 10 is defined as an X-axis, a phantom line passing through the turning axis 1 of the joint and extending perpendicular to the X-axis is defined as a Y-axis, and a bending direction of the second attachment 20 with respect to an intersection (turning axis 1) between the X-axis and the Y-axis is defined as a plus direction of the Y-axis. The turning axis 1 shows a position of the joint in a state where the second attachment 20 stretches to the utmost with respect to the first attachment 10. The turning axis 1 is displaced within a circle shown with dotted lines in FIGS. 2 and 3.

The turning fulcrum 41 of the swing arm 40 is disposed at the plus position of the Y-axis, and the one end 51 of the auxiliary artificial muscle 50 is disposed at a minus position of the Y-axis. One end 61A of the guide hole 61 is disposed at the plus position of the Y-axis, and the other end 61B of the guide hole 61 is disposed at the minus position of the Y-axis.

The first attachment 10 and the second attachment 20 are connected to each other through spring joints 70. Coil springs are used as the spring joints 70, and the spring joints 70 are extension springs. Each of the spring joints 70 is disposed such that an axis 71 of the coil spring is located at the minus position of the Y-axis in a state where the second attachment 20 stretches to the utmost with respect to the first attachment 10.

In addition, a length of each of the coil springs is adjusted such that a deviation of a rotation shaft of the spring joint 70 caused by the coil spring becomes equal to a deviation of a turning axis 1 of the joint.

It is preferable that the muscle force assisting device includes a first power source (not shown) that contracts the artificial muscle 30, and a second power source (not shown) that contracts the auxiliary artificial muscle 50. It is preferable that the artificial muscle 30 and the auxiliary artificial muscle 50 are provided on each of both sides of each arm in a pair.

As shown in FIGS. 4 and 5, a stretching-artificial muscle 80 is provided on the side of the elbow. FIG. 4 shows a state where the stretching-artificial muscle 80 is contracted to the utmost, and FIG. 5 shows a state where the stretching-artificial muscle 80 stretches to the utmost.

The operation of the muscle force assisting device according to the embodiment will be described below.

As shown in FIGS. 1(a) and 1(b), in a stretched state of the muscle force assisting device, the end of the second attachment 20 on the side opposite from the joint has an initial angle of about 10° in the plus direction of the Y-axis with respect to the first attachment 10.

In this state, the artificial muscle 30 and the auxiliary artificial muscle 50 stretch in the longitudinal direction to the utmost. The displacing end 42 of the swing arm 40 is disposed on the one end 61A of the guide hole 61.

In the state shown in FIGS. 1(a) and 1(b), a center line 70y of the spring joint 70 in its longitudinal direction is on the Y-axis, and a center 70x of an upper winding thereof in the longitudinal direction is disposed substantially at the minus position of the Y-axis.

In the state shown in FIGS. 1(a) and 1(b), FIG. 2 shows that only the artificial muscle 30 is operated by a first power source.

Since a second power source is not operated, the auxiliary artificial muscle 50 maintains the state where it stretches to the utmost in its longitudinal direction, and the displacing end 42 of the swing arm 40 is disposed on the one end 61A of the guide hole 61.

The artificial muscle 30 is operated by the first power source. With this, the artificial muscle 30 is contracted in its longitudinal direction, and the second attachment 20 is bent with respect to the first attachment 10 by the contraction of the artificial muscle 30.

In the state shown in FIGS. 1(a) and 1(b), the axis 71 of the coil spring is located in the minus position of the Y-axis, the center line 70y of the spring joint 70 in the longitudinal direction is located on the Y-axis, and the center 70x of the upper winding in the longitudinal direction is located substantially at the minus position of the Y-axis.

In the state shown in FIG. 2, a state where the auxiliary artificial muscle 50 is operated by the second power source is shown in FIG. 3.

By operating the auxiliary artificial muscle 50 by the second power source, the auxiliary artificial muscle 50 is contracted in the longitudinal direction, and the displacing end 42 of the swing arm 40 is moved to the other end 61B of the guide hole 61 by the contraction of the auxiliary artificial muscle 50.

If the displacing end 42 of the swing arm 40 moves to the other end 61B of the guide hole 61, the one end 31 of the artificial muscle 30 also moves to the other end 61B of the guide hole 61, and the second attachment 20 further bends with respect to the first attachment 10.

In the description of the operation of the embodiment, the auxiliary artificial muscle 50 is operated after the operation of the artificial muscle 30 is completed. However, at the time of the bending operation, it is only necessary that the operation of the first power source is started before the operation of the second power source is started, and the operation of the auxiliary artificial muscle 50 may be started before the operation of the artificial muscle 30 is completed.

As described above, according to the invention, the one end 31 of the artificial muscle 30 can be displaced with respect to the first attachment 10. By displacing the one end 31 of the artificial muscle 30, the bending angle of the second attachment 20 with respect to the first attachment 10 is increased as compared with a case where the one end 31 of the artificial muscle 30 is not displaced. According to the invention, the bending angle can be increased without increasing the driving force by displacing the one end 31 of the artificial muscle 30.

In the invention, the first attachment 10 includes the swing arm 40, the end of the swing arm 40 on the side opposite from the joint is the turning fulcrum 41, the end of the swing arm 40 on the side of the joint is the displacing end 42, and the one end 31 of the artificial muscle 30 is provided on the displacing end 42 of the swing arm 40. With this, the position of the one end 31 of the artificial muscle 30 can be changed.

In the invention, the one end 51 of the auxiliary artificial muscle 50 is provided on the first attachment 10, and the other end 52 of the auxiliary artificial muscle 50 is provided on the displacing end 42 of the swing arm 40. With this, the swing arm 40 can be displaced by the auxiliary artificial muscle 50, and the bending angle of the artificial muscle 30 can be increased.

In the invention, the first attachment 10 includes the guide plate 60, the guide plate 60 includes the guide hole 61, and the displacing end 42 of the swing arm 40 is displaced along the guide hole 61. With this, the displacing end 42 can stably be displaced.

In the invention, the turning fulcrum 42 of the swing arm 40 is disposed at the plus position of the Y-axis, and the one end 51 of the auxiliary artificial muscle 50 is disposed at the minus position of the Y-axis. With this, the movable range of the swing arm 40 can be increased, and the swing arm 40 can smoothly be moved by the auxiliary artificial muscle 50.

In the invention, the one end 61A of the guide hole 61 is disposed at the plus position of the Y-axis, and the other end 61B of the guide hole 61 is disposed at the minus position of the Y-axis. With this, the movable range of the swing arm 40 can be increased.

In the invention, the first attachment 10 and the second attachment 20 are connected to each other through the spring joints 70, and the coil springs are used as the spring joints 70. With this, even when the muscle force assisting device and the joint are deviated from each other, smooth motion can be secured.

In the invention, at the time of the bending motion, the one end 31 of the artificial muscle 30 is displaced after the motion of the artificial muscle 30 is started. With this, smooth motion can be carried out.

The present invention can be utilized as a muscle force assisting device that assists motion of a joint such as an elbow, a knee and a wrist.

What is claimed is:

1. A muscle force assisting device comprising
a first attachment adapted to be arranged along one bone of a joint,
a second attachment adapted to be arranged along an other bone of the joint, and
an artificial muscle having one end provided on the first attachment and having an other end provided on the second attachment, in which
an actuator that is extensible or contractible by supplying or discharging gas, liquid, solid, or a mixture thereof is used as the artificial muscle, and
the muscle force assisting device adapted to assist motion of any one of a user's elbow, knee and wrist, wherein
the one end of the artificial muscle is displaced via an auxiliary artificial muscle, and a bending angle of the second attachment with respect to the first attachment is increased as compared with a case where the one end of the artificial muscle is not displaced,
the first attachment has a swing arm,
the first attachment includes a turning fulcrum of the swing arm on a side opposite from the joint,
the first attachment includes a displacing end of the swing arm on a side of the joint,
the swing arm includes the one end of the artificial muscle on the displacing end, and
the second attachment includes the other end of the artificial muscle on the side opposite from the joint.

2. The muscle force assisting device according to claim 1, wherein the auxiliary artificial muscle having one end provided on the first attachment and having the other end provided on the displacing end of the swing arm.

3. The muscle force assisting device according to claim 2, wherein when a phantom line passing through a turning axis of the joint and extending along a longitudinal direction of the first attachment is defined as an X-axis, and a phantom line passing through the turning axis of the joint and extending perpendicular to the X-axis is defined as a Y-axis, and when one end of the second attachment with respect to an intersection between the X-axis and the Y-axis is displaced in a plus direction of the Y-axis, the turning fulcrum of the swing arm is disposed at a plus position of the Y-axis, and one end of the auxiliary artificial muscle is disposed at a minus position of the Y-axis.

4. The muscle force assisting device according to claim 2, wherein when a phantom line passing through a turning axis of the joint and extending along a longitudinal direction of the first attachment is defined as an X-axis, and a phantom line passing through the turning axis of the joint and extending perpendicular to the X-axis is defined as a Y-axis, and when one end of the second attachment with respect to an intersection between the X-axis and the Y-axis is displaced in a plus direction of the Y-axis, the turning fulcrum of the swing arm is disposed at a plus position of the Y-axis, one end of the auxiliary artificial muscle is disposed at a minus position of the Y-axis, and the displacing end of the swing arm is displaced between the plus position of the Y-axis and the minus position of the Y-axis.

5. An operating method of the muscle force assisting device described in claim 2 comprising a first power source that contracts the artificial muscle, and a second power source that contracts the auxiliary artificial muscle, wherein at a time of bending motion, operation of the first power source is started before operation of the second power source is started.

6. The muscle force assisting device according to claim 2, wherein the first attachment includes a guide plate, the guide plate includes a guide hole, and the displacing end of the swing arm is displaced along the guide hole.

7. The muscle force assisting device according to claim 1, wherein the first attachment includes a guide plate, the guide plate includes a guide hole, and the displacing end of the swing arm is displaced along the guide hole.

8. The muscle force assisting device according to claim 1, wherein the first attachment and the second attachment are connected to each other through a spring joint, and a coil spring is used as the spring joint.

* * * * *